United States Patent
Rhodes et al.

(10) Patent No.: US 8,709,091 B2
(45) Date of Patent: Apr. 29, 2014

(54) TIBIAL INSERT AND ASSOCIATED SURGICAL METHOD

(75) Inventors: James Matthew Rhodes, Warsaw, IN (US); Jordan Soonja Lee, Warsaw, IN (US)

(73) Assignee: DePuy Synthes Products, LLC, Raynham, MA (US)

( * ) Notice: Subject to any disclaimer, the term of this patent is extended or adjusted under 35 U.S.C. 154(b) by 604 days.

(21) Appl. No.: 12/496,044

(22) Filed: Jul. 1, 2009

(65) Prior Publication Data

US 2009/0270995 A1 Oct. 29, 2009

Related U.S. Application Data

(63) Continuation of application No. 11/171,802, filed on Jun. 30, 2005, now Pat. No. 7,572,293.

(51) Int. Cl.
*A61F 2/38* (2006.01)

(52) U.S. Cl.
USPC ............... 623/20.32; 623/20.3; 623/20.34

(58) Field of Classification Search
USPC ........... 623/14.12, 20.14, 20.3, 20.32–20.34
See application file for complete search history.

(56) References Cited

U.S. PATENT DOCUMENTS

| | | |
|---|---|---|
| D245,259 S | 8/1977 | Shen |
| 4,895,572 A | 1/1990 | Chernoff |
| 4,919,671 A | 4/1990 | Kemp |
| 4,978,357 A | 12/1990 | Goymann et al. |
| 5,152,797 A | 10/1992 | Luckman et al. |
| 5,171,276 A * | 12/1992 | Caspari et al. ............ 623/16.11 |
| 5,336,266 A | 8/1994 | Caspari et al. |
| 5,383,937 A * | 1/1995 | Mikhail .................... 623/20.18 |
| 5,458,653 A | 10/1995 | Davidson |
| 5,509,934 A | 4/1996 | Cohen |
| 5,549,683 A | 8/1996 | Bonutti |
| 6,102,954 A | 8/2000 | Albrektsson et al. |
| 6,139,580 A | 10/2000 | Wurzinger et al. |
| 6,217,617 B1 | 4/2001 | Bonutti |
| 6,267,785 B1 | 7/2001 | Masini |
| 6,364,910 B1 | 4/2002 | Shultz et al. |
| 6,699,289 B2 | 3/2004 | Iannotti et al. |
| 6,939,135 B2 | 9/2005 | Sapian |
| 7,041,104 B1 | 5/2006 | Cole et al. |
| 7,105,027 B2 | 9/2006 | Lipman et al. |
| 7,179,295 B2 | 2/2007 | Kovacevic |
| 7,294,149 B2 | 11/2007 | Hozack |

(Continued)

FOREIGN PATENT DOCUMENTS

| | | |
|---|---|---|
| DE | 8708501 U1 | 4/1988 |
| DE | 4219808 C1 * | 12/1993 |

(Continued)

OTHER PUBLICATIONS

Translation of DE4219808C1.*

(Continued)

*Primary Examiner* — Thomas J Sweet
*Assistant Examiner* — Megan Wolf
(74) *Attorney, Agent, or Firm* — Barnes & Thornburg LLP

(57) ABSTRACT

A tibial insert includes a platform defining an upper bearing surface and a bottom surface. A keel of the tibial insert is coupled to the bottom surface of the platform. A surgical method for knee anthroplasty is also disclosed.

16 Claims, 9 Drawing Sheets

(56) References Cited

U.S. PATENT DOCUMENTS

| | | |
|---|---|---|
| 7,615,054 B1 | 11/2009 | Bonutti |
| 2001/0037153 A1 | 11/2001 | Rockwood et al. |
| 2003/0060884 A1 | 3/2003 | Fell |
| 2003/0125809 A1 | 7/2003 | Iannotti et al. |
| 2004/0006393 A1 | 1/2004 | Burkinshaw |
| 2004/0083005 A1 | 4/2004 | Jacobsson et al. |
| 2004/0113790 A1 | 6/2004 | Hamel et al. |
| 2005/0059972 A1 | 3/2005 | Biscup |
| 2005/0125068 A1 | 6/2005 | Hozack et al. |
| 2005/0143731 A1 | 6/2005 | Justin et al. |
| 2005/0165317 A1 | 7/2005 | Turner et al. |
| 2006/0111787 A1 | 5/2006 | Ballie et al. |
| 2007/0260322 A1 | 11/2007 | Nowakowski |

FOREIGN PATENT DOCUMENTS

| | | |
|---|---|---|
| DE | 102004053075 A1 | 5/2006 |
| EP | 0290736 A1 | 11/1988 |
| EP | 0552950 A1 | 7/1993 |
| EP | 0709073 | 5/1996 |
| EP | 0925765 A2 | 6/1999 |
| EP | 1136045 | 9/2001 |
| EP | 1738718 A2 | 1/2007 |
| FR | 2698536 A1 | 6/1994 |
| WO | 9322990 A1 | 11/1993 |
| WO | 0013585 A1 | 3/2000 |
| WO | 0036998 | 6/2000 |
| WO | 0149173 A1 | 7/2001 |
| WO | 2005120203 A2 | 12/2005 |

OTHER PUBLICATIONS

European Search Report for European Patent Application No. 06253071.2-2310, Nov. 8, 2006, 6 pgs.

"The Natural-Knee Unicompartmental System," The Comprehensive Natural-Knee Family, 2005 Zimmer, Inc., www.zimmer.com, 4 pgs.

"User Friendly Instrumentation," M/G Unicompartmental Knee System, 2005, Zimmer, Inc., www.zimmer.com, 3 pgs.

Preservation UNI-Compartmental Knee Surgical Technique Booklet, DePuy Orthopaedics, Inc., 2002, Rev. 2.

"Zimmer Travecular Metal Femoral Cone Augment Surgical Technique Surgical Technique Booklet," Zimmer, Inc. 2005, 10 pgs.

"Surgical Technique for Nexgen Primary Porous Patella with Trabecular Metal Surgical Technique Booklet," Zimmer, Inc., 2001, 16 pgs.

"Surgical Technique for Nexgen Curciate Retaining (CR) and Legacy Knee Posterior Stabilized (LPS) Trabecular Metal Monoblock Tibias," Zimmer, Inc., 2003, 11 pgs.

"MOST Options—Limb Salvage Surgery," Zimmer, Inc., 2005, 2 pgs.

"LCS/UNI Unicompartmental Knee System with Porocoat Porous Coating Surgical Technique Booklet," DePuy Orthopaedics, Inc., 1998, 14 pgs.

"Zimmer MOST Options System," Zimmer, Inc., 2006, 1 pg.

"Comprehensive Sizing—Patient-Specific Results, Zimmer Unicompartmental High Flex Knee System—Built on Success," Zimmer, Inc., 2005, 3 pgs.

European Search Report for European Application No. 07251541.4-2310, Aug. 16, 2007, 5 pages.

European Search Report for European Application No. 07251541.4-2310, Nov. 5, 2007, 8 pages.

European Search Report for European Application No. 07252482.0-5121, Mar. 11, 2009, 3 pages.

European Search Report for European Application No. 07252488.7-2310, Nov. 15, 2007, 7 pages.

European Search Report for European Application No. 07252484.6-2310, Dec. 20, 2007, 10 pages.

* cited by examiner

TIBIAL INSERT AND ASSOCIATED SURGICAL METHOD

This application is a continuation of U.S. patent application Ser. No. 11/171,802, filed on Jun. 30, 2005 now U.S. Pat. No. 7,572,293, which is incorporated in its entirety herein by reference. Cross-reference is made to U.S. patent application Ser. No. 11/425,936 titled TIBIAL INSERT AND METHOD FOR IMPLANTING THE SAME by James Matthew Rhodes and Jordan Soonja Lee; U.S. patent application Ser. No. 11/425,929 titled TIBIAL INSERT HAVING A REINFORCED KEEL by James Matthew Rhodes and Jordan Soonja Lee; U.S. patent application Ser. No. 11/425,921 titled TIBIAL INSERT HAVING MULTIPLE KEELS by James Matthew Rhodes and Jordan Soonja Lee; U.S. patent application Ser. No. 11/425,947 titled TIBIAL INSERT HAVING A KEEL INCLUDING A BORE FORMED THEREIN by James Matthew Rhodes and Jordan Soonja Lee, each of which is assigned to the same assignee as the present application and each of which is hereby incorporated by reference.

FIELD OF THE DISCLOSURE

The present disclosure relates generally to orthopaedic prostheses, and particularly to tibial inserts and methods of using the same.

BACKGROUND

During the lifetime of a patient, it may be necessary to perform a joint replacement procedure on the patient as a result of, for example, disease or trauma. For example, many knee replacement surgeries are performed each year. Total knee replacement or arthroplasty may involve replacement of the mid-shaft portion of the femur, proximal, distal, and/or total femur, and proximal tibia. Unicompartmental knee replacement or arthroplasty involves unicondylar resurfacing. Unicompartmental knee arthroplasty provides an alternative to total knee arthroplasty for rehabilitating knees when only one condyle has been damaged as a result of trauma or disease such as noninflammatory degenerate joint disease or its composite diagnosis of osteoarthritis or post-traumatic arthritis, for example. As such, unicompartmental knee arthroplasty may be indicated for use in patients undergoing surgery for a severely painful and/or disabled joint damaged as a result of osteoarthritis, traumatic arthritis, rheumatoid arthritis, or a failed previous implant when only one condyle of the knee (medial or lateral) is affected. Further, unicompartmental knee replacements may be "multi-piece" replacements wherein a unicompartmental tibial insert is used to replace each of the medial and lateral condyles of the patient. A single, total femoral component or two partial femoral components may be used to cooperate with the two unicompartment inserts.

Unicompartmental knee replacements are intended to provide increased patient mobility and reduce pain by replacing the damaged knee joint articulation in patients where there is evidence of sufficient sound bone to seat and support the components. Age and activity level factor into all reconstructive procedures and the state of the arthritis determines the treatment. With the advancement of minimally invasive techniques that support unicompartmental knee reconstruction, a growing number of patients are offered this alternative for relief from the disabling pain of arthritis and for the potential benefits of a rapid recovery. Many technical challenges persist, however, with respect to providing less invasive unicompartmental knee surgeries.

SUMMARY

According to one aspect of the present disclosure, a tibial insert includes a platform including an upper bearing surface and a keel extending downwardly from the platform. The keel includes a first downwardly-extending surface and a second downwardly-extending surface. The keel further includes a rounded, distal surface defining a continuous radius connecting the first downwardly-extending surface to the second downwardly-extending surface. The keel is generally cylindrical in shape and further includes an anterior/posterior length greater than a height of the keel.

The keel may include a narrow neck portion coupled to the platform and a rounded base portion coupled to the narrow neck portion. Additionally, the keel may include a first channel defined in one of the first downwardly-extending surface, the second downwardly-extending surface, and the rounded, distal surface. The first channel may extend along at least a portion of the anterior/posterior length of the keel. The keel may further include a second channel also defined in one of the first downwardly-extending surface, the second downwardly-extending surface, and the rounded, distal surface. The second channel may extend along at least a portion of the anterior/posterior length of the keel. The keel may further include a plurality of auxiliary channels each in communication with at least one of the first and second channels.

The platform of the insert may include a recessed portion defined in the bottom surface of the platform. The platform may also include an inner wall defining the recessed portion. A portion of the inner wall may be wavy. The recessed portion may include a first recessed area positioned laterally from the keel and a second recessed area in fluid communication with the first recessed area and positioned medially from the keel.

The platform may further include a passageway defined by a first opening into the recessed portion and a second opening formed in an outboard wall of the platform. Additionally, the platform may include an outboard surface or wall and an inboard surface or wall. The second opening of the passageway may be formed in an anterior portion of the outboard wall of the platform.

According to another aspect of the present disclosure, a tibial insert includes a platform including an upper bearing surface and a bottom surface and a keel extending in an anterior/posterior direction on the platform. The bottom surface of the platform includes a first recessed area positioned laterally from the keel and a second recessed area positioned medially from the keel. The first and second recessed areas are in fluid communication with each other. The platform may further include an outboard wall and a passageway extending between a first opening into at least one of the first and second recessed areas and a second opening formed in the outboard wall. Illustratively, the passageway may extend between and open into the second recessed area and an anterior portion of the outboard wall.

The keel of the tibial insert may include a plurality of channels defined therein. The plurality of channels may include a first plurality of channels extending along an anterior/posterior length of the keel and a second plurality of channels each in fluid communication with at least one of the first plurality of channels.

According to still another aspect of the present disclosure, a tibial insert includes a platform including an upper bearing surface and a bottom surface, a keel coupled to the platform and positioned to extend along an anterior/posterior length of the platform, a recessed portion formed in the bottom surface of the platform, and a passageway having a first opening in communication with the recessed portion and a second opening formed in an outboard wall of the platform.

The platform may include a wavy inner wall formed defining at least a portion of one of the first and the recessed areas.

According to yet another aspect of the present disclosure, a surgical method for knee arthroplasty is provided to replace at least a portion of one or more condyles of a patient's tibia. The surgical method may include the steps of drilling a hole in a condyle of the tibia, inserting an elongated, cylindrical pin into the hole drilled in the condyle, resecting at least a portion of the condyle to create a surgically-prepared, generally horizontal surface and a surgically-prepared, generally vertical surface. The surgical method may also include the steps of removing the pin from the hole drilled in the condyle, forming a slot in the surgically-prepared, horizontal surface such that the slot extends posteriorly from an opening formed in an anterior surface of the tibia, and inserting a tibial insert through the opening formed in the anterior surface of the tibia and into the slot formed in the surgically-prepared, horizontal surface.

The resecting step may include advancing a surgical saw medially from an outer, lateral surface of the condyle to contact the pin and advancing the surgical saw inferiorly from a superior surface of the condyle to contact the pin. Further, the forming step may include forming a first downwardly-extending surface, a second downwardly-extending surface, and a rounded, distal surface defining a continuous radius connecting the first and second downwardly-extending surfaces. The surgical method may further comprise the step of injecting bone cement into the slot after the inserting step.

According to still another aspect of the present disclosure, a surgical method for knee arthroplasty may include the steps of resecting at least a portion of a condyle of a patient's tibia to create a surgically-prepared tibial surface, positioning a tibial insert on the surgically-prepared tibial surface, and injecting bone cement into a space between the surgically-prepared tibial surface and the tibial insert. The positioning step may include forming a slot in the surgically-prepared tibial surface such that the slot extends posteriorly from an opening formed in an anterior surface of the tibia. The positioning step may further include inserting a keel of a tibial insert through the opening formed in the anterior surface of the tibia and into the slot formed in the surgically-prepared tibial surface.

Further, the injecting step may include injecting bone cement into the slot formed in the surgically-prepared tibial surface. The injecting step may further include injecting bone cement through a passageway of the tibial insert formed between the space and an outboard wall of the tibial insert.

The resecting step may include drilling a hole in the condyle, inserting an elongated cylindrical pin into the hole drilled in the condyle, advancing a surgical saw medially from a lateral surface of the tibia to contact the pin, and advancing the surgical saw inferiorly from a superior surface of the condyle to contact the pin.

According to yet another aspect of the present disclosure, a surgical method for knee arthroplasty to replace at least a portion of one or more condyles of a patient's tibia includes the steps of resecting at least a portion of the condyle to create a surgically-prepared, horizontal surface and a surgically-prepared vertical surface of the resected condyle, forming a slot in the surgically-prepared, horizontal surface such that the slot extends posteriorly from an opening formed in an anterior surface of the tibia, and inserting a keel of a tibial insert through the opening formed in the anterior surface of the tibia and into the slot formed in the surgically-prepared, horizontal surface.

BRIEF DESCRIPTION OF THE DRAWINGS

The detailed description particularly refers to the accompanying figures in which.

DETAILED DESCRIPTION OF THE DRAWINGS

Figure 1:
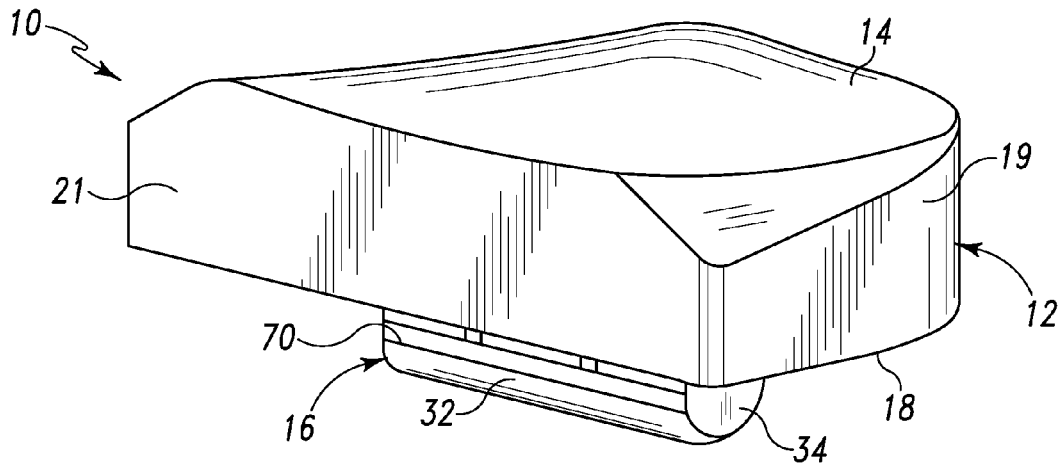
FIG. 1 is a perspective view of a unicompartmental tibial insert.

While the concepts of the present disclosure are susceptible to various modifications and alternative forms, specific exemplary embodiments thereof have been shown by way of example in the drawings and will herein be described in detail. It should be understood, however, that there is no intent to limit the disclosure to the particular forms disclosed, but on the contrary, the intention is to cover all modifications, equivalents, and alternatives following within the spirit and scope of the invention as defined by the appended claims.

As shown in FIGS. 1-4, a tibial insert 10 includes a platform 12 defining an upper bearing surface 14 and a keel 16 coupled to a lower surface 18 of the platform 12 and extending downwardly from the platform 12. Illustratively, the tibial insert 10 is a unicompartmental tibial insert intended to replace only one of the two condyles 20 of a tibia 22, as shown in FIG. 5, for example. In other words, the tibial insert 10 may be used by a surgeon or other technician during a unicompartmental knee arthroplasty (UKA) whereas other tibial inserts (not shown) may be used to replace both condyles 20 of a tibia during a total knee arthroplasty (TKA). Illustratively, the insert 10 as well as other tibial inserts disclosed herein are suitable for use or implantation by surgeons adopting either conventional or minimally invasive surgical methods of performing UKA. Further, although the tibial insert 10 is a unicompartmental tibial insert, it is within the scope of this disclosure that the various features associated with the tibial insert 10, as discussed below, may also be associated with tibial inserts typically used during TKA to replace both condyles of the tibia.

Figure 2:
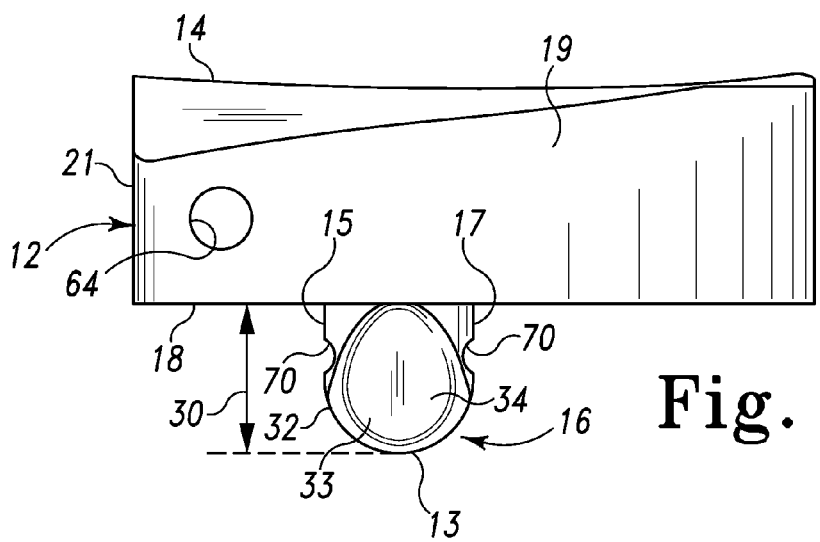
FIG. 2 a front view of the tibial insert of FIG. 1.
Figure 3:
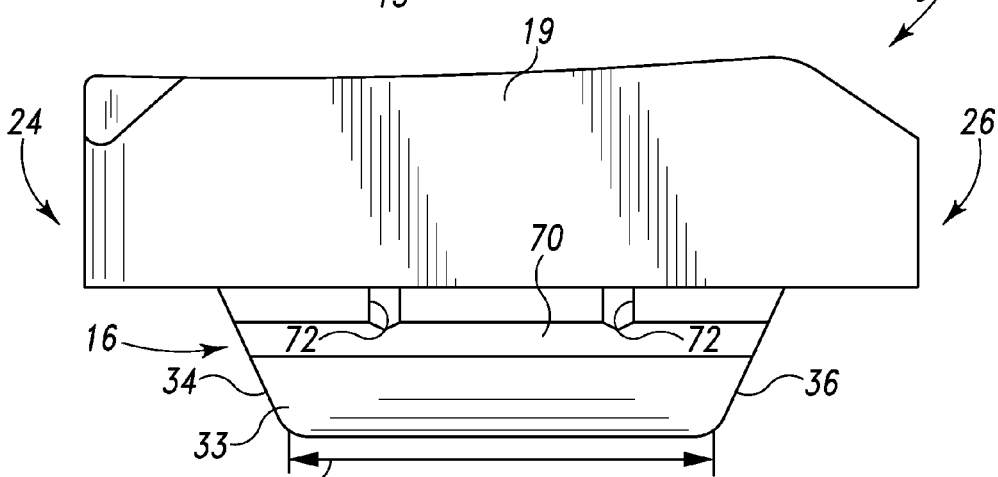
FIG. 3 is a side view of the tibial insert of FIGS. 1 and 2 showing a keel of the insert extending between anterior and posterior portions of the insert.

Looking again to FIGS. 1-4, the tibial insert 10 includes the platform 12 and the keel 16 coupled or secured to the platform 12. The platform 12 is generally "D-shaped" and includes the upper bearing surface 14, the lower surface 18, a curved, outer or outboard surface 19, and an inner or inboard surface 21. The keel 16 extends in an anterior/posterior direction on the tibial insert 10 between an anterior (or front) side 24 of the tibial insert 10 and a posterior (or back) side 26 of the tibial insert. Illustratively, the keel 16 is generally centrally positioned between the anterior and posterior sides 24, 26 of the platform 12. Illustratively, the keel 16 is elongated and generally cylindrical in shape and is dimensioned such that an anterior/posterior length 28 of the keel 16 (as shown in FIG. 3) is greater than a height 30 of the keel 16 (as shown in FIG. 2). Illustratively, the anterior/posterior length 28 of the keel 16 is measured along the distal-most portion of the keel 16 and the height 30 is measured from the bottom surface 18 of the platform 12 to the distal-most portion of the keel 16.

Figure 7:
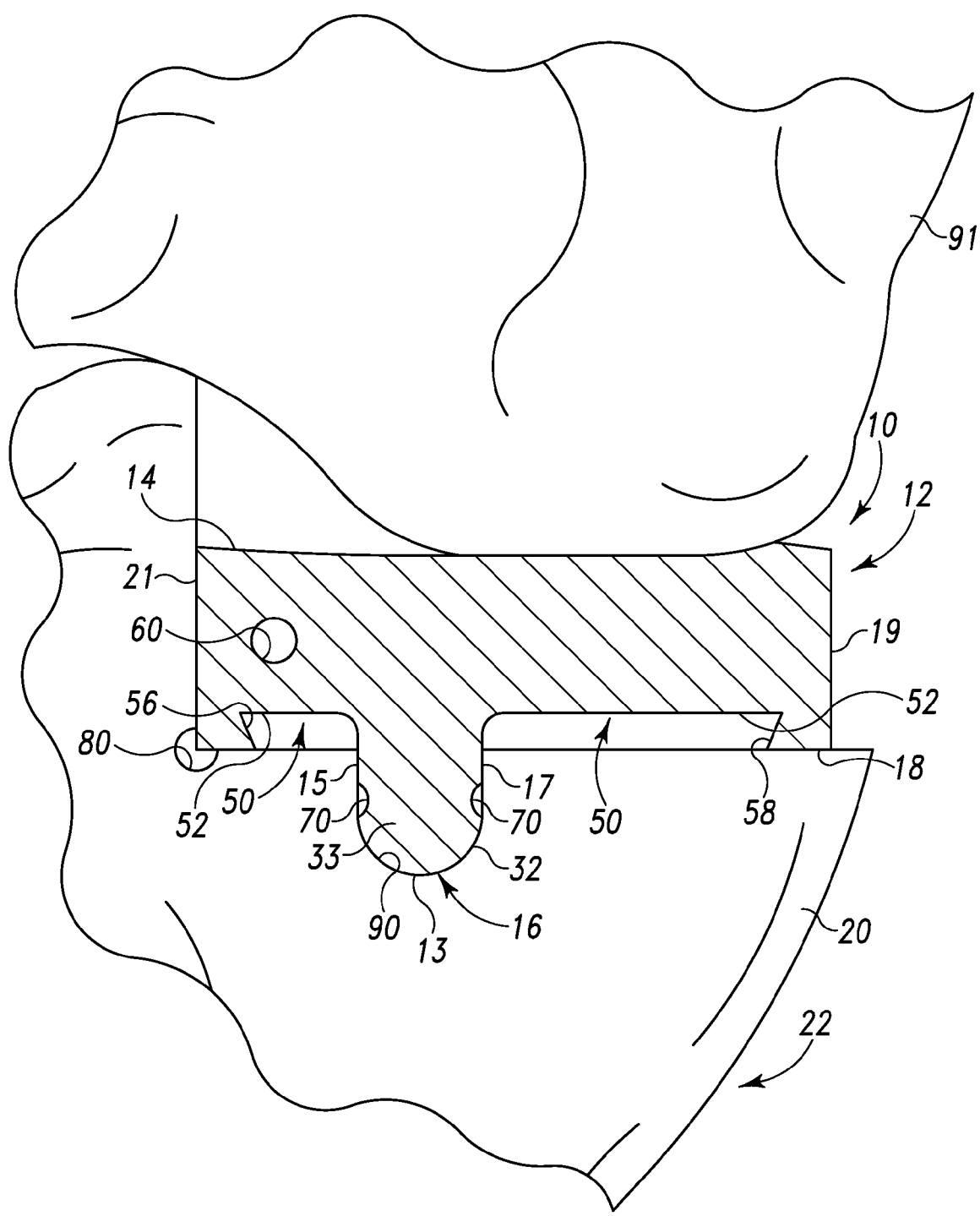
FIG. 7 is a sectional view of the tibial insert of FIGS. 1-4 positioned within the slot formed in the tibia.

A cross-section of the keel 16, as shown in FIG. 7, is generally "U-shaped" to define an outer, curved wall 32 of the keel 16 having rounded edges. Specifically, the keel 16 includes a rounded distal end 33 which defines a generally semi-circular shape in cross-section. In other words, a portion of the keel 16, and specifically the distal end 33 of the keel 16, forms or defines a 180° arc. As such, the keel includes a first generally downwardly-extending surface 15 extending perpendicularly from the lower surface 18 to a first distal-most point, a second generally downwardly-extending surface 17 extending perpendicularly from the lower surface 18 to a second distal-most point, and a rounded, distal surface 13 defining a continuous radius connecting the first and second downwardly-extending surfaces 15, 17. The distal surface 13 extends longitudinally in the anterior/posterior direction parallel to the lower surface 18 of the platform 12. Illustratively, this rounded shape may aide in preventing stress risers from forming in the tibia 22 when the insert 10 is implanted into the tibia 22, as discussed in greater detail below. Stress risers in the tibia 22 combined with forces generated by the keel 16 of the tibial insert 10 may cause the tibia 22 to fracture. The rounded keel 16 of the implant 10 may reduce the risk of such stress risers forming.

Looking to FIGS. 1-4, both an anterior end or face 34 of the keel 16 and a posterior face 36 of the keel 16 is chamfered to create an angled surface. These angled surfaces 34, 36 may aide a surgeon performing a traditional or conventional UKA in downwardly inserting the keel 16 into a predrilled slot formed in the tibia 22. As mentioned above and discussed in more detail below, the tibial insert 10 of the present disclosure is suitable for use with surgeons performing UKA using both conventional or minimally invasive surgical methods. Further, although the anterior and posterior face 34, 36 of the keel 16 is angled, it is within the scope of this disclosure for the insert to include a keel having a generally vertical anterior face and generally vertical posterior face as well.

Figure 4:
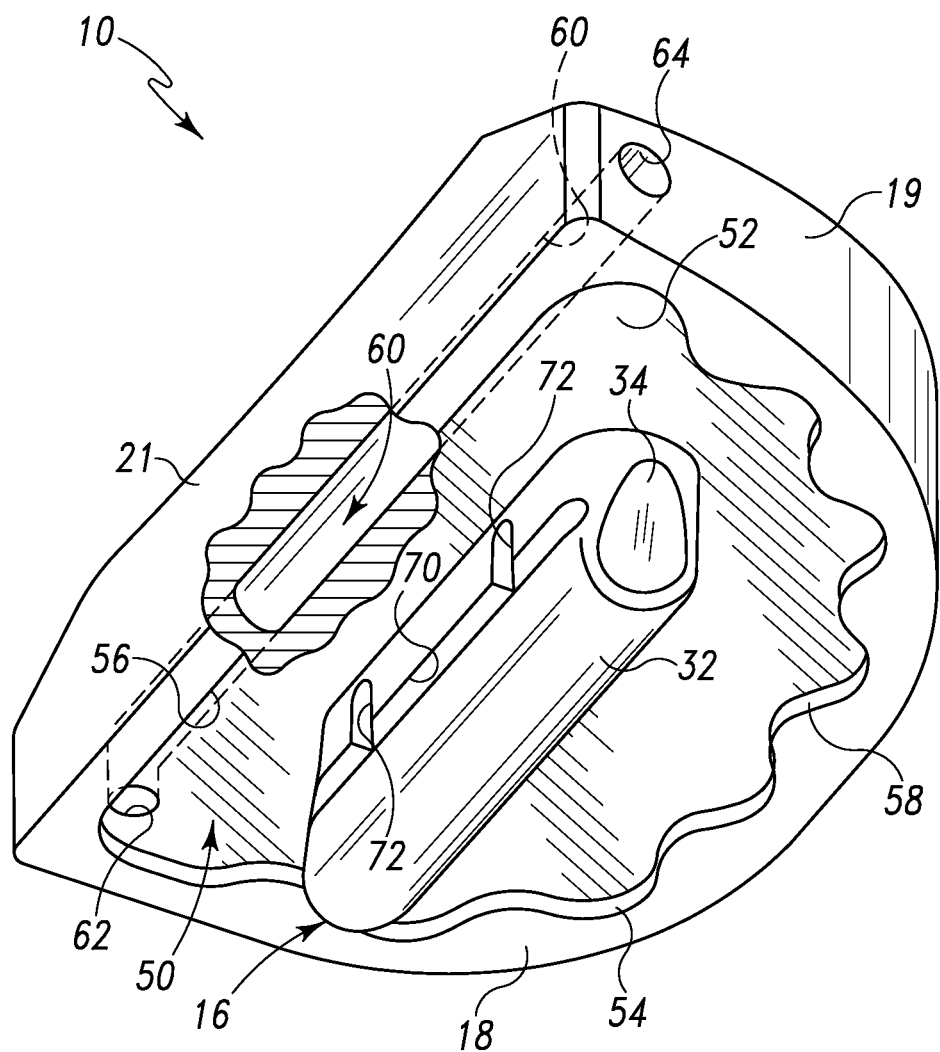
FIG. 4 is a bottom perspective view of the tibial insert of FIGS. 1-3 showing a recessed portion or cement pocket formed in a bottom surface of a platform of the tibial insert and further showing an air evacuation passageway (in phantom) formed through the platform.
Figure 5:
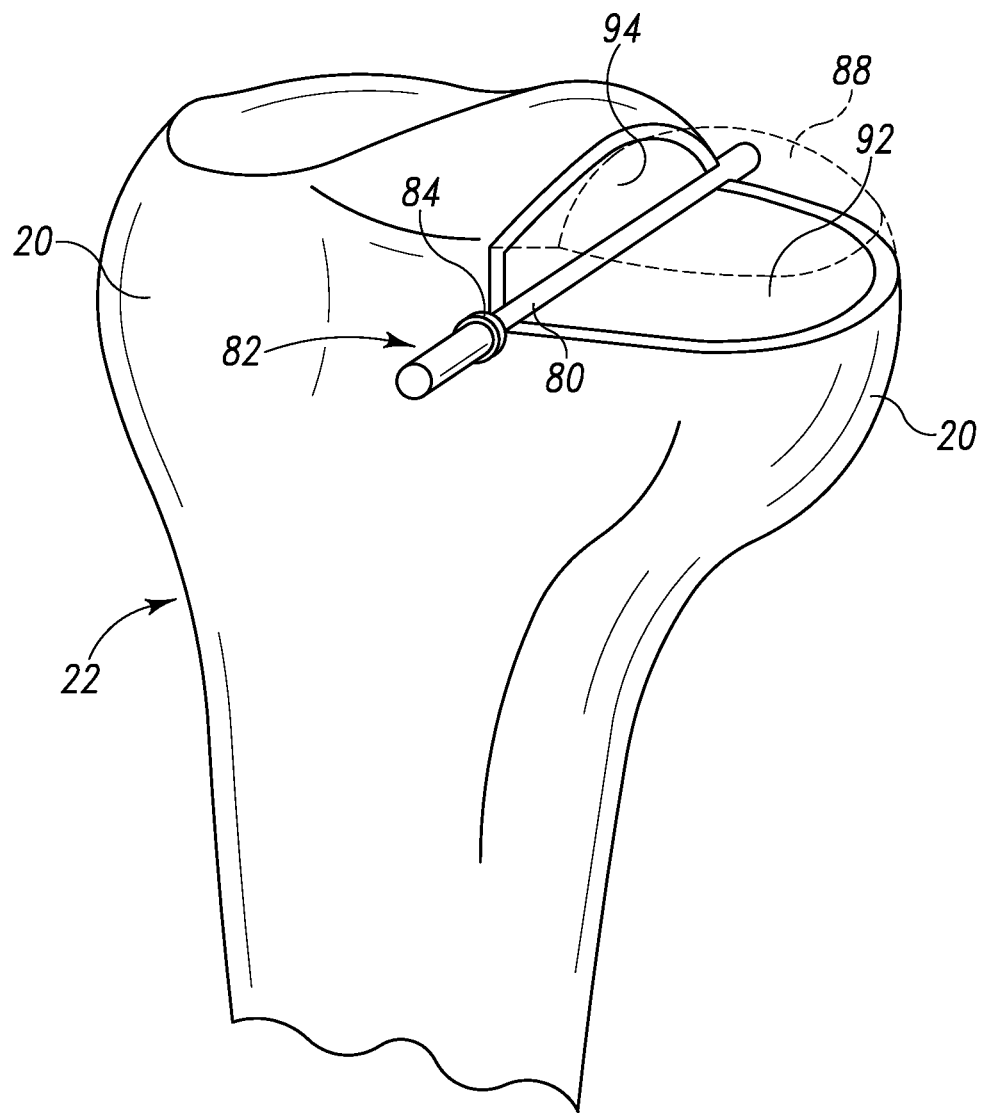
FIG. 5 is a perspective view of a portion of a tibia showing a reference pin having been inserted into a pre-drilled hole in the tibia and further showing (in phantom) one of the condyles of the tibia having been partially resected to create a surgically-prepared, horizontal surface and a surgically-prepared, vertical surface.

Looking now to FIG. 4, the tibial insert 10 includes a recessed portion or cement pocket 50 formed within the bottom surface 18 of the platform 12 to create a recessed bottom surface 52 of the platform 12. The keel 16 extends downwardly from the recessed bottom surface 52. As shown in FIG. 4, an inner wall 54 of the platform 12 defines the recessed portion 50 and includes an inner wall portion 56 and an outer wall portion 58. Illustratively, while both the inner and outer wall portions 56, 58 define an angled surface (as shown best in FIG. 7), the inner wall portion 56 is straight and extends in a generally straight, anterior/posterior direction. Further, the outer wall portion 58 is wavy and extends in a generally curved direction. Illustratively, the inner wall portion 56 may be wavy and/or the curved, outer side wall portion 58 may be straight. The wavy shape of the inner wall portion 56 and/or the outer wall portion 58 increases the amount of surface area of the inner wall 54 defining the recessed portion and may, therefore, provide for increased fixation of the bone cement to the insert and the tibia. The angled surface of the inner wall 54 provides a greater surface area to allow the bone cement injected into the cement pocket 50 to adhere to the inner wall 54. As is discussed in further detail below, the cement pocket 50 may take on various shapes and sizes.

As further shown in FIG. 4, an air evacuation passageway 60 (shown in phantom) is formed within the platform 12 of the tibial insert 10. A first opening 62 of the passageway 60 is formed in the recessed bottom wall 52 of the platform 12 while a second opening 64 of the passageway 60 is formed in the curved, outboard surface 19 of the platform 12. The air evacuation passageway 60 includes a first passageway that extends from the second opening 64 in the anterior-posterior direction toward the first opening 62 and a second passageway that extends from the first opening 62 to the first passageway to fluidly couple the recessed portion 50 to the second opening 64. Illustratively, the second opening 64 of the passageway 60 is formed within the anterior side 24 of the curved, outboard surface 19 of the platform 12. Further, the first opening 62 may be formed in any suitable portion of the recessed bottom wall 52 of the recessed portion 50 such that the passageway 60 is in fluid communication with the recessed portion 50. As is discussed in greater detail below, the air evacuation passageway 60 allows air trapped within the recessed portion 50 of the insert 10 to be evacuated as bone cement (not shown) is injected around the insert 10 once the insert 10 has been implanted into the tibia 22.

Looking again to both FIGS. 1-4, the keel 16 of the tibial insert 10 includes a horizontally extending cement channel 70 formed in each downwardly-extending surface 15, 17 of the rounded outer wall 32 of the keel 16 and generally extends along the anterior/posterior length 28 of the keel 16. Illustratively, each cement channel 70 may run along the entire anterior/posterior length 28 of the keel 16 or simply along a portion of the length 28 of the keel 16. Each anterior/posterior cement channel 70 may be considered to be a main cement channel.

Further, as shown best in FIGS. 3 and 4, two secondary or branch cement channels 72 are also formed in each downwardly-extending surface 15, 17 of the outer wall 32 of the keel 16. Illustratively, each secondary channel 72 extends generally vertically off each respective main channel 70. As such, the secondary channels 72 are in communication with each respective main channel 70. Therefore, as discussed in greater detail below, bone cement injected into each main channel 70 will also flow into the respective secondary or auxiliary channels 72. Although one main cement channel 70 is formed in each side of the outer surface 32 of the keel 16, it is within the scope of this disclosure for the keel 16 to include any number of cement channels extending along the anterior/posterior length 28 of the keel 16.

For example, the entire outer surface 32 (including each side or downwardly-extending surface 15, 17 of the keel 16 and the rounded, distal surface 13 of the keel 16) may include one or more cement channels formed therein. The keel 16 may only include a single cement channel as well. Further, any number of secondary cement channels 72 may be formed off of any of the various main cement channels 70 the keel 16 may include. The secondary cement channels 72 may connect adjacent main cement channels 72 as well to define an interconnected network of cement channels. Further, the secondary cement channels 72 may run vertically or at a ninety-degree angle to the main cement channel(s) or may extend at any other angle in relation to the main cement channel(s). In other words, the keel 16 may include any combination and number of main cement channels and/or secondary cement channels positioned to run in any straight, curved, or wavy direction and formed in the outer surface 32 of the keel 16. These cement channels may or may not be interconnected with each other.

As discussed above, the tibial insert 10 is used primarily in unicompartmental knee arthroplasty (UKA) and may be implanted into a patient's tibia 22 using traditional or conventional UKA surgical methods as well as more minimally invasive methods. Oftentimes a large incision is required to access the knee joint in the more conventional UKA surgical methods. Further, conventional UKA surgical methods may require that the knee joint be flexed to allow room to implant the insert 10. For example, in many traditional methods of implantation, the insert is pressed downwardly onto the resected or partially resected tibia which may create another potential for generating stress risers in the tibia 22.

Figure 6:
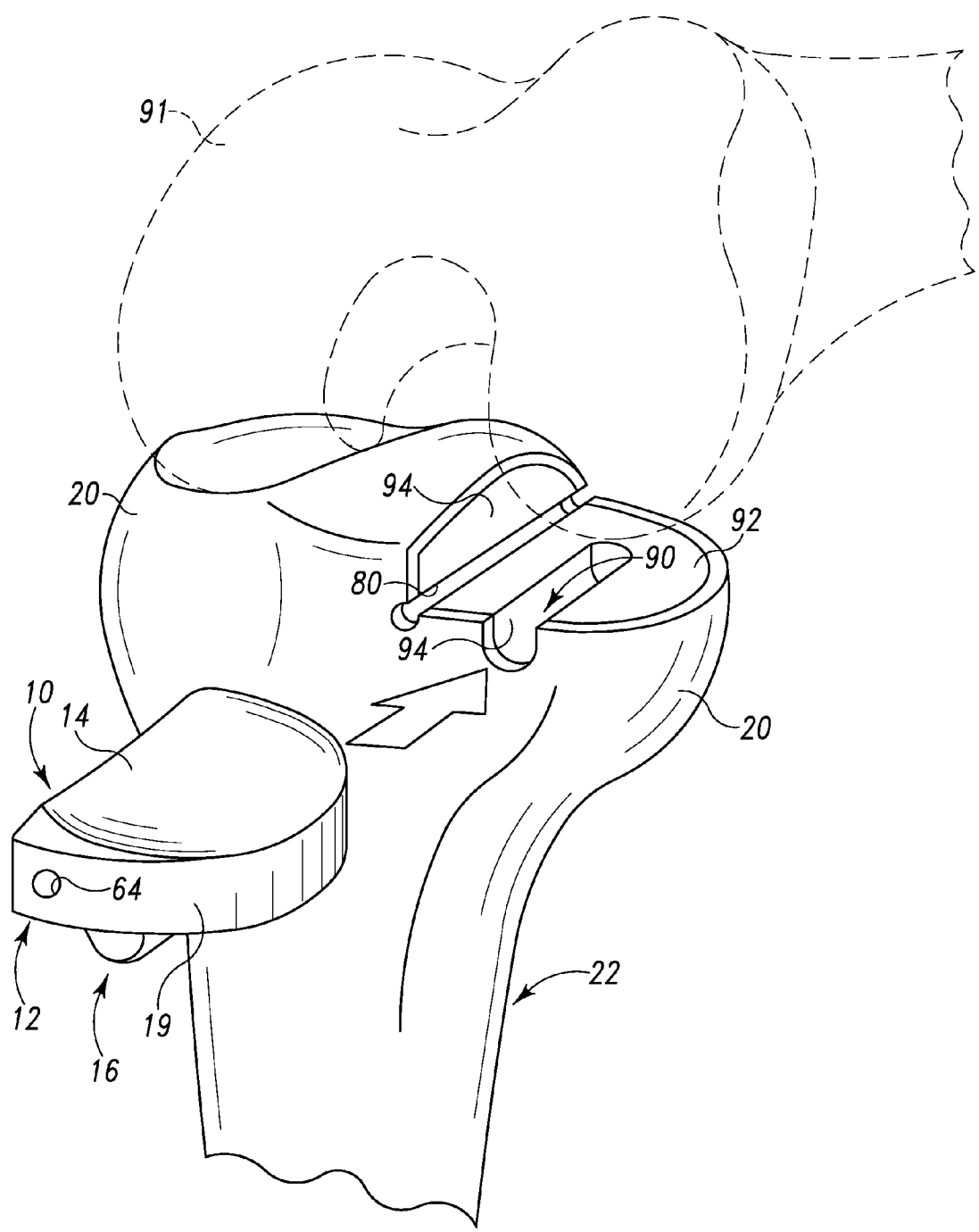
FIG. 6 is a perspective view of the tibia of FIG. 5 and the tibial insert of FIGS. 1-4 showing an anterior slot formed in the surgically-prepared, horizontal surface of the tibia for receiving the keel of the tibial insert.

In addition to the various traditional methods of total and partial knee arthroplasties, the tibial insert 10 may be implanted using reduced or minimally invasive methods, as shown in FIGS. 5-7, for example. Initially, the surgeon creates an incision through patient's skin and anterior to the patient's tibia 22 to provide anterior access to the patient's tibia 22. Once the surgeon has gained anterior access to the tibia 22, a surgical drill (not shown) is used to drill a reference hole 80 through the particular condyle 20 to be replaced, as shown in FIG. 5. Illustratively, the reference hole 80 extends between the anterior and posterior portions of the condyle 20.

Once the reference hole 80 has been drilled, a reference pin or stop pin 82 is inserted into the hole 80. Illustratively, the stop pin 82 includes an outer rim or lip 84 near one end of the pin 82 to prevent the surgeon or other technician from over-inserting the pin 82 within the reference hole 80. The pin 82, therefore, is sized to be inserted into the pre-drilled hole 80 and the rim 84 of the pin 82 is slightly larger than the reference hole 80 to prevent the pin 82 from being inserted further within the hole 80. The position of the reference hole 80 is determined by the surgeon or other technician on a case-by-case basis depending upon a number of different factors including, for example, the shape of the patient's tibia, the amount of damage to the particular condyle being replaced during the UKA, the shape of the implant, etc.

Once the stop pin 82 has been inserted into the reference hole 80, a surgical saw or osteotome (not shown) is used to resect at least a portion of the patient's condyle in order to remove a damage portion 88 of the condyle 20. The surgical saw also creates a surgically-prepared, generally horizontal surface 92 and a surgically-prepared generally vertical surface 94. As the osteotome cuts through the condyle 20 both horizontally and vertically, the osteotome runs into the stop pin 82 and is thereby prevented from moving further through the condyle 20 in that particular direction. Illustratively, the osteotome is advanced medially from an outer, lateral surface of the condyle 20 to contact the stop pin 82 and is advanced inferiorly from an outer, superior surface of the condyle 20 to contact the stop pin 82. The stop pin 82, therefore, acts as a saw blade guide and as a stop for the surgeon operating the osteotome to prevent the osteotome from cutting portions of the condyle 20 beyond the stop pin 82. Further, using the stop pin 82 as a guide prevents the bone cuts created by the osteotome from intersecting or crisscrossing each other. Such crisscrossed bone cuts may increase the risk of stress risers forming in the tibial 22 which may then cause the tibia 22 to fracture. It is also within the scope of the disclosure to remove the stop pin 82 once one of the two surfaces 92, 94 have been prepared by the surgical saw. For example, the surgeon may prepare the horizontal surface 92, remove the stop pin 82, and then prepare the vertical surface 94, or visa versa.

Once the appropriate saw cuts have been made through the condyle 20 and the damaged portion 88 of the condyle 20 has been removed, the stop pin 82 may be removed from the reference hole 80. The resected condyle 20 is now defined by the surgically-prepared, generally horizontal surface 92 and the surgically-prepared, generally vertical surface 94. As shown in FIG. 6, the reference hole 80 is generally cylindrical in shape and therefore forms no sharp edges or corners. Such rounded corners of the reference hole 80 may further disseminate the stresses in the tibia 22 and may act to prevent or reduce stress risers from forming.

After the stop pin 82 has been removed from the reference hole 80, another surgical drill (not shown) is used to form a slot 90 in the tibia 22, as shown in FIG. 5. The slot 90 is oriented anteriorly and is formed in the horizontal surface 92 of the resected tibia 22. Looking to FIG. 6, the anterior slot 90 extends posteriorly from an opening formed in an anterior surface of the tibia 22. Illustratively, the slot 90 terminates before reaching the posterior face of the tibia 22. The termination of the slot 90 prior to reaching the posterior face of the tibia 22 may prevent posterior leakage of bone cement injected between the implanted insert 10 and the tibia 22.

The slot 90 may be drilled or cut using a drill, a saw or osteotome, or other suitable instrument. Generally, the size of the anterior slot 90 is slightly larger than that of the keel 16 of the insert 10. The anterior slot 90 is generally cylindrical in shape and, like the reference hole 80 is rounded and does not form any sharp edges or corners. In other words, an inner surface 94 of the resected condyle 20 defining the anterior slot 90 is rounded or curved. The anterior slot 90 is sized to receive the keel 16 of the implant 10. As such, a distal or bottom portion of the rounded surface 94 of the anterior slot 90 forms a 180° arc and is semi-circular in shape when viewed in cross-section. Further, slot 90 includes a first downwardly-extending surface, a second downwardly-extending surface, and a rounded, distal surface defining a continuous radius connecting the first and second downwardly-extending surfaces. Further, similar to the rounded, distal end 33 of the keel 16, the rounded distal surface 94 of the slot 90 may aid in dispersing the stresses created on the tibia 22 from the keel 16 of the implanted insert 10.

Looking now to FIGS. 6 and 7, once the stop pin 82 has been removed from the reference hole 80 and the anterior slot 90 has been drilled, the tibial insert 10 is inserted into place within the resected portion of the condyle 20. In particular, the keel 16 of the tibial insert 10 is inserted through the opening formed in the anterior surface of the tibia 22 and into the slot 90 formed in the surgically-prepared horizontal surface 92. Anteriorly sliding the insert 10 into the anterior slot 90, rather than pressing the insert 10 downwardly onto the anterior slot, may allow the surgeon or technician to use a small or minimal anterior incision formed in the patient's knee. Illustratively, the insert 10 may be anteriorly slid into the slot 90 formed in the condyle 20 both when the knee joint is flexed (as shown in FIG. 6 where a femur 91 of the patient is flexed backward relative to the tibia 22) or when the knee joint is extended (as shown in FIG. 7). Further, although the insert 10 is shown to be slid anteriorly with the slot 90 through a minimal incision, for example, the insert 10 may also be implanted into the tibia 22 and positioned within a slot, such as slot 90, formed in the resected condyle 20 of the tibia 22 using conventional or traditional surgical UKA methods.

As shown in FIG. 6, the keel 16 of the insert 10 is sized and shaped to fit within the anterior slot 90 drilled within the horizontal surface 92 of the resected portion of the tibia 22. The combination of the rounded outer surface 32 of the keel 16 and the rounded inner wall 94 defining the anterior slot 90 cooperate to evenly distribute stresses on the patient's knee to reduce stress risers or stress concentrations from forming in the tibia 22. Illustratively, once the insert 10 has been fully implanted within the tibia 22, the bottom surface 18 of the platform 12 of the insert 10 is adjacent to and generally engages the resected horizontal surface 92 of the tibia 22.

Prior to sliding the keel 16 of the insert 10 into the anterior slot 90, the anterior slot 90 may be filled with bone graft material (not shown) to grow into the solid bone of the tibia 22 and form a strong bond between the keel 16 of the insert 10 and the tibia 22. As discussed above, an anterior end of the keel 16, 116 of the respective inserts 10, 110 is set back from an anterior end of the platform 12 of each respective insert 10, 110. As such, once the insert has been fully implanted, a space is provided within the anterior slot between the anterior end of the keel and the anterior side of the tibia. As such, once the insert 10 has been implanted, a surgeon may fill the open anterior end of the anterior slot 90 (between the anterior face of the tibia 22 and the anterior surface 34 of the keel 16) with bone graft material to form grow into the tibia 22 and potentially further reduce the risk of fractures.

Once the insert 10 has been properly implanted and positioned within the resected tibia 22, bone cement (not shown) may be injected through the opening formed in the anterior face of the tibia 22 and into the channels 70, 72 within the keel 16 and the recessed portion 50 formed in the platform 12. The channels 70, 72 and recessed portion 50 collectively form spaces between the tibia 22 and the insert 10. Therefore, a surgeon or other technician may inject bone cement into the anterior slot 90 to fill the channels 70, 72 and recessed portion 50. Illustratively, the wavy lateral wall portion 58 of the recessed portion 50 defines a greater surface area than a non-wavy wall portion, for example, to which the bone cement may adhere. This greater surface area created by the wavy lateral wall portion 58 may increase fixation of the bone cement to the insert 10.

During surgery, the bone cement injected into the anterior slot 90 is generally contained within the channels 70, 72 and the resected portion 50 of the insert 10 to aid in preventing the bone cement from posteriorly oozing out of these cement pockets or spaces to help eliminate any posterior clean-up of the excess bone cement. For example, it may be difficult for a surgeon implanting the insert 10 using minimally invasive surgical methods to clean or remove any posterior overflow of the bone cement due to the fact that the surgeon may only be provided with anterior access to the tibia 22 and the insert 10 via the anterior incision.

The air evacuation passageway 60 formed in the platform 12 allows air within the cement pocket areas 70, 72, 50 to exit out the second opening 64 of the passageway (formed in the anterior side of the outboard surface 19 of the platform) as the bone cement fills the cement pocket areas 70, 72, 50. Illustratively, it is contemplated that a surgeon or technician may inject bone cement into the anterior slot 90 until bone cement begins to fill the air evacuation passageway 60 and is seen to exit the second opening 64 of the passageway 60. Seeing the bone cement fill the air evacuation passageway 60 and exit the second opening 64 of the passageway 60 may be an indication to the surgeon or other technician that the cement pocket areas 70, 72, 50 have been sufficiently filled with bone cement. Although the bone cement is injected into the grooves the keel after the insert has been properly implanted and positioned within the resected tibia, it is also within the scope of this disclosure to insert bone cement into the predrilled anterior slot before the insert is implanted.

Figure 8:
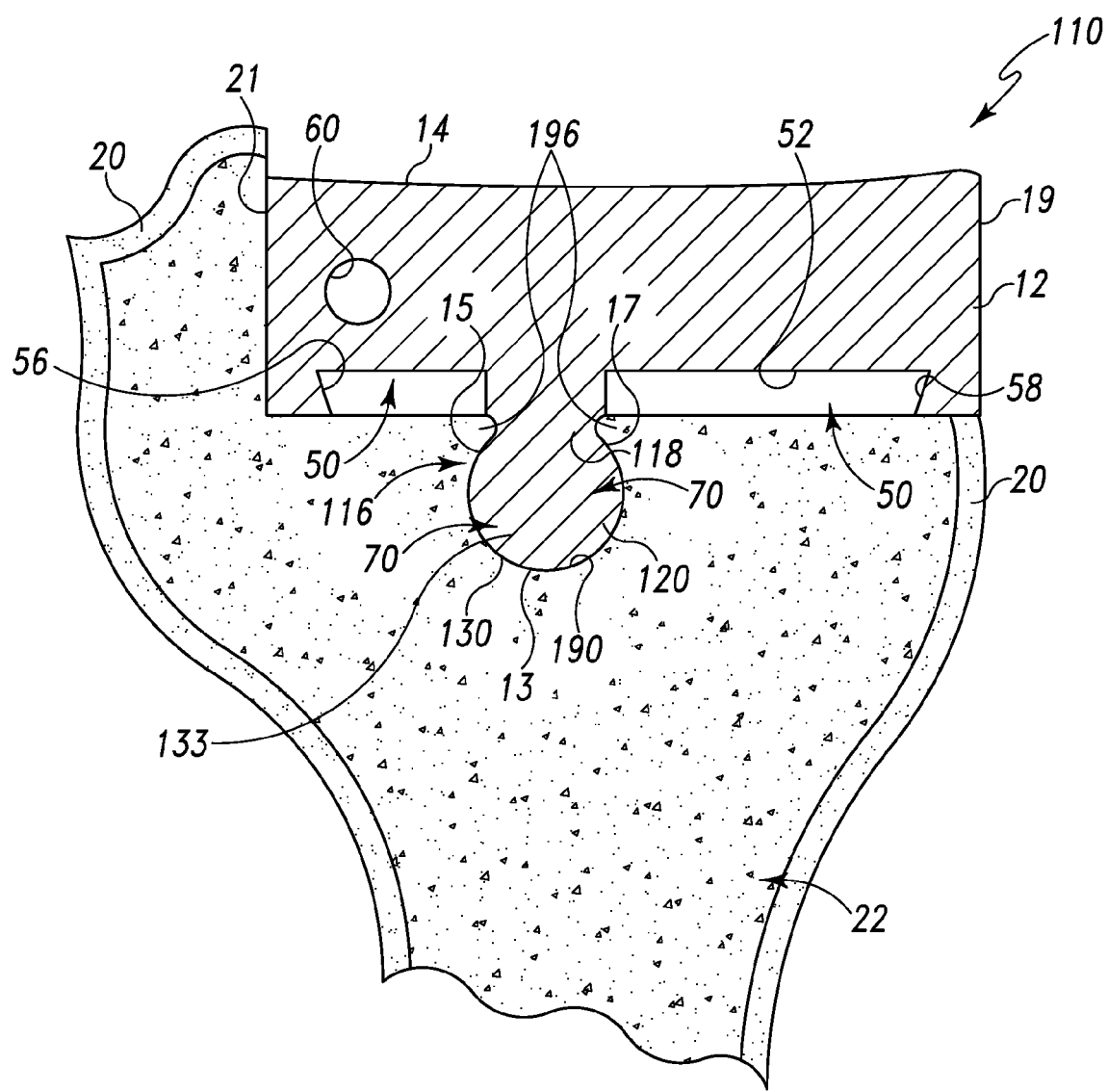
FIG. 8 is a sectional view of an alternative tibial insert positioned within an alternative anterior slot formed in the surgically-prepared, horizontal surface of the tibia.

Looking now to FIG. 8, an alternative tibial insert 110 is provided. Various features of the tibial insert 110 are the same as or similar to corresponding features of the insert 10 and, therefore, are represented by like reference numerals. The alternative tibial insert 110 includes a rounded keel 116 similar to the keel 16 of the tibial insert 10. However, the rounded keel 116 includes a narrow, neck portion 118 coupled to the bottom of the platform 12 of the insert 110 and a wider body or base portion 120 coupled to the narrow, neck portion 118. Illustratively, an outer surface 130 of the keel 116 is rounded. Specifically, as discussed above with respect to the keel 16 of the insert 10, the keel 116 includes a rounded distal end 133 which defines a 180° arc and is semi-circular in shape when viewed in cross-section. Further, the keel 116 includes a first generally downwardly-extending surface 15, a second generally downwardly-extending surface 17, and a rounded, distal surface 13 defining a continuous radius connecting the first and second downwardly-extending surfaces 15, 17. As is discussed below, the shape of the body portion 120 of the rounded keel 116 and the narrow neck portion 118 creates a rounded locking joint between the tibial insert 110 and the resected tibia 22 to prevent the implanted insert 110 from being able to be moved upwardly out of the anterior slot 190 formed in the tibia 22.

An alternative anterior slot 190 has been drilled in the resected tibia 22 which is sized to fit the shape of the rounded locking keel 116. Illustratively, a cross-section of an inner surface of the anterior slot 190 is generally "C-shaped" (as shown in FIG. 8), whereas a similar cross-section of the anterior slot 90 is generally "U-shaped" (as shown in FIG. 7). A distal portion of the anterior slot 190 also defines a 180° arc and a semi-circular shape when viewed in cross-section and further defines first and second downwardly-extending surfaces and a rounded, distal surface defining a continuous radius connecting the first and second downwardly extending surfaces. Although the distal ends 33, 133 of both keels 16, 116 as well as the distal portions of each respective anterior slot 90, 190 form 180° arcs to define a semi-circular shape, it is within the scope of this disclosure to include rounded keels defining other arc angles as well.

Looking again to FIG. 8, the C-shaped anterior slot 190 illustratively forms two opposite overhang or lip portions 196 within the resected condyle 20. Illustratively, the distance between such portions 196 is smaller than a diameter or width of the body portion 120 of the rounded keel 116. As such, a locking connection between the slot 190 and the keel 116 is created when the rounded keel 116 is anteriorly slid into place within the slot 190 of the resected portion of the condyle 20. This locking connection between the rounded keel 116 and the anterior slot 190 prevents the tibial insert 110 from being moved upwardly out of the desired implanted position shown in FIG. 8. As discussed above, the rounded shape of both the keel 116 and the slot 190 is maintained to reduce the potential for stress risers and bone fractures from forming.

Figure 9:
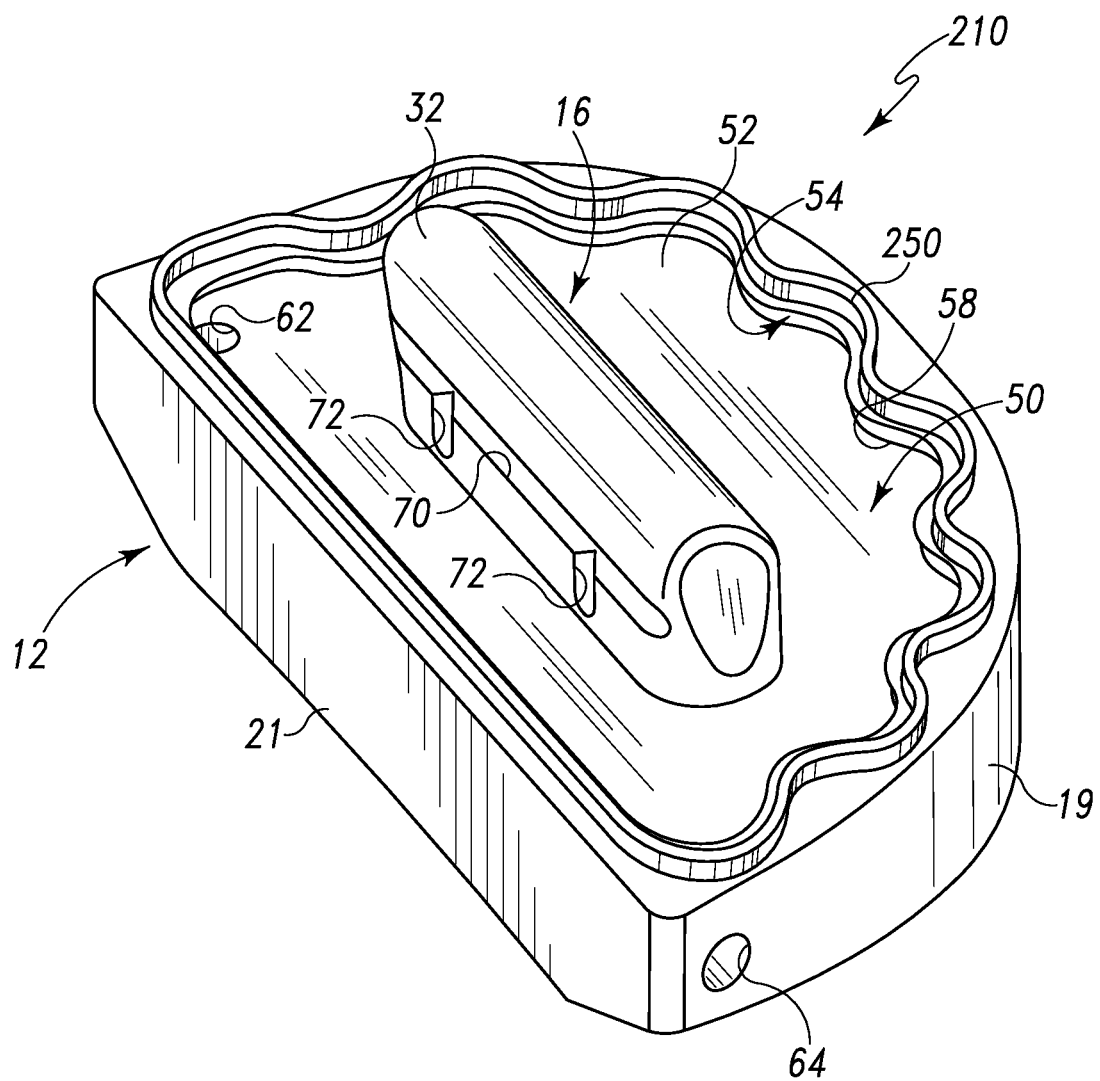
FIG. 9 is a bottom perspective view of yet another tibial insert similar to the tibial insert of FIGS. 1-4 and including a cement seal or ridge extending from the bottom surface of the platform around the cement pocket formed in the platform.
Figure 10:
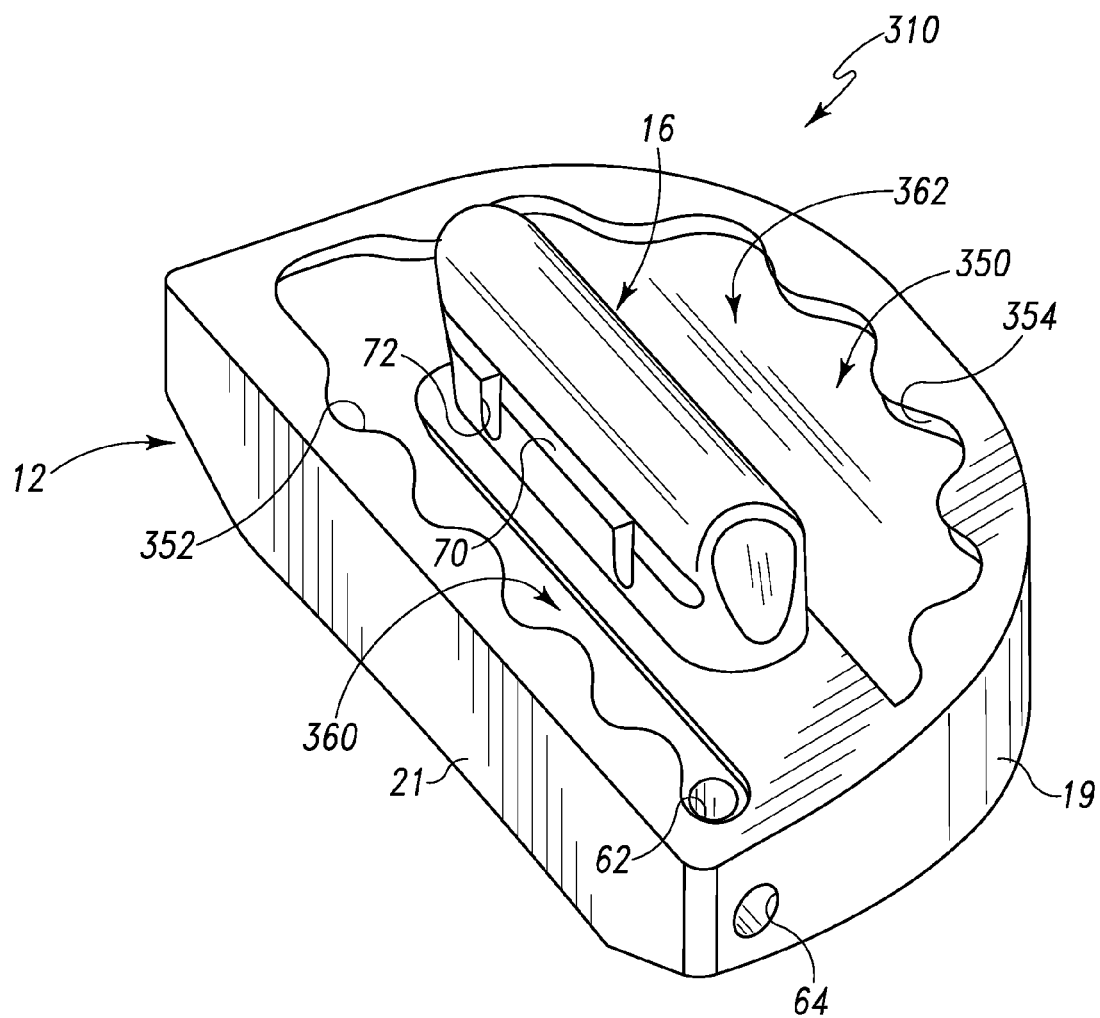
FIG. 10 is a bottom perspective view of yet another tibial insert showing an alternative cement pocket of the tibial insert.
Figure 11:
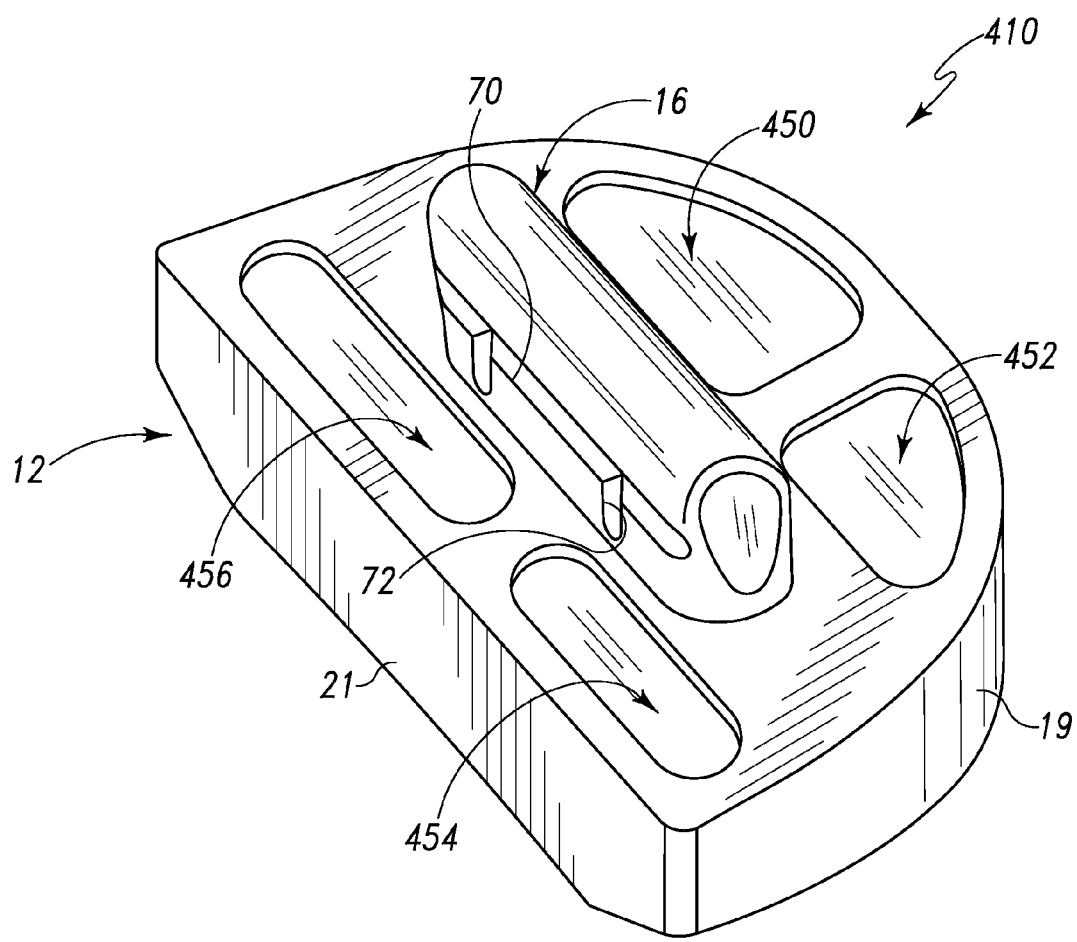
FIG. 11 is a bottom perspective view of yet another tibial insert showing four separate cement pockets of the tibial insert.

Looking now to FIGS. 9-11, additional tibial inserts 210, 310, and 410 are provided. Tibial inserts 210, 310, and 410 include the same or similar features of tibial inserts 10 and 110; as such, like reference numerals have been used for like components. Looking first to FIG. 9, the tibial insert 210 includes a cement ridge or seal 250 coupled to and extending outwardly from the bottom surface 18 of the platform 12. Illustratively, the cement ridge 250 is positioned around the recessed portion 50 and is provided to form a seal around the recessed portion 50 to help contain bone cement injected into the recessed portion 50, as discussed above. Illustratively, once the tibial insert 210 has been properly implanted and positioned within the resected tibia 22, a surgeon or other technician may then exert a downward force on the insert 210 to cause the cement ridge 250 of the insert 210 to be pressed into the horizontal surface 92 of the resected tibia 22. As such, the cement ridge 250 works to contain bone cement which has been injected into the anterior slot 90 formed in the resected condyle 20 and to prevent this bone cement from oozing out beyond the inner wall 54 of the recessed portion 50, for example.

Looking now to FIG. 10, the tibial insert 310 includes an alternative recessed portion 350. Recessed portion 350 is defined by a medial inner wall portion 352 and a lateral inner wall portion 354. Illustratively, both the medial and lateral inner wall portions 352, 354 are wavy. Further illustratively, the keel 16 of the insert 310 is coupled to the bottom surface 18 of the platform 12 (rather than being coupled to the recessed bottom surface 52 of the recessed portion 350. As such, the recessed portion or area 350 of the insert 310 defines a medial or first recessed portion 360 and a lateral or second recessed portion 362 in fluid communication with the medial recessed portion 360. Illustratively, the first opening 62 of the air evacuation passageway 60 is formed at an anterior end of the medial recessed portion 360.

Finally, looking to FIG. 11, the tibial insert 410 includes four separate recessed areas 450, 452, 454, 456 formed in the bottom surface 18 of the platform 12. Illustratively, a first pair of the recessed areas 450, 452 are positioned laterally from the keel 16 while a second pair of the recessed areas 454, 456 are positioned medially from the keel 16. As shown in FIG. 11, the recessed areas 450, 452, 454, 456 are not in fluid communication with each other. Although not shown, an air evacuation passageway may be provided between each of the recessed areas 450, 453, 454, 456 and an anterior portion of the outboard surface 19 of the platform 12.

Illustratively, the tibial inserts 10, 110, 210, 310, and 410 disclosed herein may include platforms having a skirt overlay such that portions of the platform may lay over and adjacent the outer surface of the tibia of the patient, for example. Further, the tibial inserts 10, 110, 210, 310, and 410 may include inlay portions coupled to the platform and/or keel of the respective inserts which lay into the surgically-prepared horizontal and/or surgically-prepared vertical surfaces of the tibia.

Further illustratively, the tibial inserts 10, 110, 210, 310, 410 disclosed herein are made from a polyethylene and may be made from UHMWPE (ultra-high molecular weight polyethylene), for example. However, the tibial inserts 10, 110, 210, 310, 410 may also be made from other materials suitable for implantation into the human body.

Further, although the tibial inserts 10, 110, 210, 310, and 410 of the present disclosure are shown and described as unitary or monolithic components, it is within the scope of this disclosure to include tibial inserts including multiple components. For example, a tibial insert of the present disclosure may include a tray component and a bearing component molded to the tray or separate from the tray for cooperation with the tray. Either the tray component or the bearing component may be made from metal, polyethylene, and/or a combination of metal and polyethylene. Illustratively, therefore, the term tibial insert hereby includes both unitary tibial inserts and tibial inserts having separate tray and bearing components.

It is further within the scope of this disclosure to include tibial inserts including reinforced rods or stiffeners through portions of the platform and/or keel of such inserts. For example, a solid metal rod may be positioned through the keel along the anterior/posterior length of the keel. Such a metal rod may be positioned through portions of the platform in any direction. The reinforcing rods may be made from metal or other suitable materials as well.

Further, a hollow reinforcing tube may be positioned through the keel of a tibial insert along the anterior/posterior length of the keel. The reinforcing tube may include apertures formed in an outer surface of the tube along the tube. Illustratively, once the insert is implanted and properly positioned, a surgeon or other technician may inject bone cement into the reinforcing tube. Bone cement injected into the reinforcing tube may exit the tube through the apertures formed in the outer surface of the tube. The keel of such an insert may further include passageways in communication with the tube and with outer channels of the keel such that bone cement injected into the tube may travel through the passageways formed in the keel to the outer channels of the keel.

Further according to the present disclosure, a tibial insert may include an alternative "interrupted" keel such that a surgeon may insert a screw or other reinforcement structure medially from an lateral side of the tibia past the keel and in the same plane as the keel. In other words, the keel may be designed with clearance to allow the surgeon to insert such a reinforcement structure. For example, the keel may include one or more holes formed through a medial/lateral width of the keel for receiving the reinforcement structure, or screw, therethrough. In another embodiment, the keel may define two discrete structures with a connecting bridge therebetween such that the space between the two structures defines the necessary clearance for the reinforcement structure described above.

Illustratively, the keel of each of the inserts 10, 110, 210, 310, and 410 disclosed herein is generally positioned to lie in an anterior/posterior direction and is generally parallel to the inboard surface of the platform of each insert. It is within the scope of this disclosure, however, to include an insert having a keel positioned to lie at an angle relative to the inboard wall of the platform. In other words, the inboard wall of the platform and the keel of the insert may not be parallel to each other. For example, the keel may extend from in an anterior/lateral position to a posterior/medial position or visa versa. As such, the corresponding slot formed in the surgically-prepared horizontal surface of the tibia my be positioned accordingly.

According to still another aspect of the present disclosure, a tibial insert of the present disclosure may include two or more keels extending from a bottom surface of the platform of each respective insert. For example, an illustrative insert may include keels parallel to each other and/or parallel to the inboard wall of the platform. Further, one or more of the keels may be angled with respect to the inboard wall of the platform as discussed above. Multiple keels may provide increased stiffness and rigidity of the insert.

Finally, it is within the scope of the present disclosure to implant a tibial insert into a tibia wherein the cross-sectional shape of the keel does not precisely match the cross-sectional shape of the slot formed in the surgically-prepared horizontal surface of the tibia. In other words, it is not necessary that the cross-sectional shape of the keel match or correspond to the cross-sectional shape of the slot into which the keel will be inserted.

While the concepts of the present disclosure have been illustrated and described in detail in the drawings and foregoing description, such an illustration and description is to be considered as exemplary and not restrictive in character, it being understood that only the illustrative embodiments have been shown and described and that all changes and modifications that come within the spirit of the disclosure are desired to be protected.

There are a plurality of advantages of the present disclosure arising from the various features of the apparatus and methods described herein. It will be noted that alternative embodiments of the apparatus and methods of the present disclosure may not include all of the features described yet still benefit from at least some of the advantages of such features. Those of ordinary skill in the art may readily devise their own implementations of an apparatus and method that incorporate one or more of the features of the present disclosure and fall within the spirit and scope of the present disclosure.

The invention claimed is:

1. An orthopaedic prosthesis comprising:
 a unicompartmental tibial insert comprising:
  a platform including an upper bearing surface and a bottom surface, the bottom surface having a recessed pocket defined therein, and
  a substantially U-shaped keel extending downwardly from the platform,
  wherein the substantially U-shaped keel includes (i) a first downwardly-extending surface extending perpendicularly from the bottom surface of the platform to a distal-most point, the first downwardly-extending surface having a first channel defined therein extending in the anterior-posterior direction and a pair of auxiliary channels defined therein extending perpendicular to the first channel, each of the auxiliary channels being in fluid communication with the first channel and the recessed pocket such that the recessed pocket is fluidly coupled to the first channel, (ii) a second downwardly-extending surface extending perpendicularly from the bottom surface of the platform to a distal-most point, and (iii) a rounded, distal surface defining an arc of about 180-degrees connecting the first and second downwardly-extending surfaces, the arc defining a continuous radius extending from the distal-most point of the first downwardly-extending surface to the distal-most point of the second downwardly-extending surface.

2. The orthopaedic prosthesis of claim 1, wherein:
 the keel further includes a second channel defined in the second downwardly-extending surfaces of the keel, and
 the second channel extends along at least a portion of the second downwardly-extending surfaces of the keel.

3. The orthopaedic prosthesis of claim 2, wherein the keel further includes a plurality of auxiliary channels, each of the auxiliary channels being in fluid communication with the second channel.

4. The orthopaedic prosthesis of claim 3, wherein:
 the keel includes an anterior end, and
 the first channel and the second channel extend from the anterior end of the keel.

5. The orthopaedic prosthesis of claim 1, wherein the platform further includes:
 a bottom wall positioned between the upper bearing surface and the bottom surface, the bottom wall being positioned parallel to the bottom surface and having a first opening defined therein,
 an inner wall extending downwardly from the bottom wall, the inner wall and the bottom wall defining the recessed pocket of the platform.

6. The orthopaedic prosthesis of claim 5, wherein the platform further includes:
 an outboard surface extending from the upper bearing surface to the bottom surface, the outboard surface having a second opening defined therein positioned above the inner wall, and
 a passageway extending from the first opening of the bottom wall to the second opening of the outboard surface.

7. The orthopaedic prosthesis of claim 6, wherein:
 the first opening is defined in a posterior portion of the bottom wall, and
 the second opening is defined in an anterior portion of the outboard surface of the platform.

8. The orthopaedic prosthesis of claim 7, wherein the inner wall and the bottom wall define an acute angle therebetween.

9. The tibial insert of claim 1, wherein the rounded, distal surface of the substantially U-shaped keel longitudinally extends in an anterior-to-posterior direction parallel to the bottom surface of the platform.

10. A tibial insert comprising:
 an upper bearing surface,
 a bottom surface positioned below the upper bearing surface,
 a bottom wall positioned between the upper bearing surface and the bottom surface, the bottom wall having a first opening defined therein,
 an inner wall extending upwardly from the bottom surface to the bottom wall,
 an outboard surface extending from the upper bearing surface to the bottom surface, the outboard surface having a second opening defined therein positioned above the inner wall, and
 a keel positioned below the bottom surface, the keel extending in an anterior-to-posterior direction and having a first channel defined therein extending in the anterior-posterior direction and a second channel defined therein in fluid communication with the first channel,
 wherein (i) the inner wall and the bottom wall cooperate to define a recessed pocket that is in fluid communication with the second channel such that the recessed pocket is fluidly coupled to the first channel, (ii) a first passageway extends from the second opening defined in the outboard surface in the anterior-posterior direction, and (iii) a second passageway extends from the first opening defined in the bottom wall to the first passageway to fluidly couple the recessed pocket with the second opening defined in the outboard surface.

11. The tibial insert of claim 10, wherein the recessed pocket includes a first recessed area and a second recessed area, and
 (i) the first recessed area being positioned laterally from the keel,
 (ii) the second recessed area being positioned medially from the keel, and
 (iii) the second recessed area being in fluid communication with the first recessed area.

12. The tibial insert of claim 11, wherein the first opening of the bottom wall is positioned in at least one of the first and second recessed areas.

13. The tibial insert of claim 10, wherein the keel includes a plurality of channels defined therein, the plurality of channels including the first channel and the second channel.

14. The tibial insert of claim 10, wherein the keel is substantially U-shaped and extends downwardly from the bottom surface, wherein the keel includes (i) a first downwardly-extending surface, (ii) a second downwardly-extending surface opposite to and substantially parallel with the first downwardly-extending surface, and (iii) a rounded, distal surface defining a continuous radius, the rounded distal surface having a first end directly connected to a distal-most point of the first downwardly-extending surface and a second end directly connected to a distal-most point of the second downwardly-extending surface of the substantially U-shaped keel, and wherein the rounded, distal surface of the substantially U-shaped keel longitudinally extends in an anterior-to-posterior direction parallel to the bottom surface and the continuous radius defines an arc of about 180-degrees.

15. The tibial insert of claim 10, wherein the keel is substantially U-shaped and extends downwardly from the bottom surface, and wherein the keel includes (i) a first downwardly-extending surface extending perpendicularly from the bottom surface to a distal-most point, (ii) a second downwardly-extending surface extending perpendicularly from the bottom surface to a distal-most point, and (iii) a rounded, distal surface defining an arc of about 180-degrees connecting the first and second downwardly-extending surfaces, the arc defining a continuous radius extending from the distal-most point of the first downwardly-extending surface to the distal-most point of the second downwardly-extending surface, and wherein the first downwardly-extending surface has formed therein a first channel extending in the anterior-posterior direction and a second channel in fluid communication with the first channel.

16. A unicompartmental tibial insert comprising:
 a platform including an upper bearing surface and a bottom surface, the bottom surface having a recessed pocket defined therein, and
 a substantially U-shaped keel extending downwardly from the platform, the substantially U-shaped keel including (i) a first downwardly-extending surface, (ii) a second downwardly-extending surface opposite to and substantially parallel with the first downwardly-extending surface, and (iii) a rounded, distal surface defining a continuous radius, the rounded, distal surface having a first end directly connected to a distal-most point of the first downwardly-extending surface and a second end directly connected to a distal-most point of the second downwardly-extending surface of the substantially U-shaped keel,
wherein the rounded, distal surface of the substantially U-shaped keel longitudinally extending in an anterior-to-posterior direction parallel to the bottom surface of the platform and the continuous radius defining an arc of about 180-degrees.

\* \* \* \* \*